(12) United States Patent
Sasaki et al.

(10) Patent No.: US 7,342,505 B2
(45) Date of Patent: Mar. 11, 2008

(54) GAS DETECTION APPARATUS AND METHOD FOR CONTROLLING GAS SENSOR

(75) Inventors: Takashi Sasaki, Saitama (JP); Hidetoshi Oishi, Saitama (JP); Takashi Saito, Saitama (JP); Akihiro Suzuki, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 266 days.

(21) Appl. No.: 11/281,772

(22) Filed: Nov. 17, 2005

(65) Prior Publication Data

US 2006/0113198 A1    Jun. 1, 2006

(30) Foreign Application Priority Data

Nov. 26, 2004    (JP)    ............... 2004-343172

(51) Int. Cl.
*G08B 17/10*    (2006.01)
(52) U.S. Cl. .................. 340/632; 340/507; 73/1.06; 73/23.31
(58) Field of Classification Search ................ 340/632, 340/633, 634, 438, 439, 501, 507, 522; 73/1.02, 73/1.06, 19.01, 23.2, 23.31; 701/108
See application file for complete search history.

(56) References Cited

U.S. PATENT DOCUMENTS

| 5,684,248 | A | * | 11/1997 | Iwata ........................ 340/438 |
| 5,772,965 | A | * | 6/1998 | Kato et al. ................. 73/23.31 |
| 5,838,243 | A | * | 11/1998 | Gallo ........................ 340/632 |
| 5,847,271 | A | * | 12/1998 | Poublon et al. ............. 340/438 |
| 5,857,163 | A | * | 1/1999 | Trombley et al. ........... 701/108 |
| 6,649,041 | B2 | * | 11/2003 | Hashimoto et al. ......... 701/109 |
| 6,850,165 | B2 | * | 2/2005 | Sakanushi et al. .......... 340/633 |
| 6,976,382 | B2 | * | 12/2005 | Kadowaki et al. ........... 73/1.06 |
| 2001/0039825 | A1 | * | 11/2001 | Kurokawa et al. ........... 73/23.2 |
| 2004/0025856 | A1 | * | 2/2004 | Iida et al. .................. 731/1.06 |
| 2005/0155405 | A1 | | 7/2005 | Sasaki et al. |
| 2007/0010932 | A1 | * | 1/2007 | Gotoh et al. ................ 73/1.06 |

FOREIGN PATENT DOCUMENTS

| CA | 2 485 604 | 11/2003 |
| EP | 1 505 385 | 2/2005 |
| JP | 06-223850 | 8/1994 |
| JP | 2004-251862 | 9/2004 |
| WO | WO 03/096000 | 11/2003 |

* cited by examiner

*Primary Examiner*—John Tweel, Jr.
(74) *Attorney, Agent, or Firm*—Fish & Richardson P.C.

(57) ABSTRACT

A first gas sensing element is provided in a first position to measure a concentration of a gas continuously, and a second sensing element is provided in a second position to measure the concentration of the gas intermittently. The second position is in close proximity to the first position. A deterioration determination unit is connected with the first and second sensing elements to make a determination as to whether the first sensing element becomes deteriorated, by comparing output values from the first and second sensing elements. A power controller is configured to supply the second sensing element with electric power throughout waiting periods during which the second sensing element stops measuring the concentration of the gas, and an amount of the electric power supplied throughout waiting periods is smaller than that supplied throughout operating periods during which the second sensing element continuously measures the concentration of the gas.

20 Claims, 11 Drawing Sheets

GAS DETECTION APPARATUS AND METHOD FOR CONTROLLING GAS SENSOR

BACKGROUND OF THE INVENTION

This invention relates to a gas detection apparatus and a method for controlling a gas sensor.

In general, a polymer electrolyte fuel cell is provided in the form of a fuel cell stack comprised of a plurality of stacked single cells each having an anode (fuel pole), a cathode (oxygen pole), and a solid polymer electrolyte membrane sandwiched between the anode and the cathode. The anode is supplied with hydrogen as a fuel, and the cathode is supplied with air as an oxidant, so that hydrogen ions produced by catalytic reaction at the anode pass through the solid polymer electrolyte membrane to the cathode in which the hydrogen ions and the oxygen react electrochemically to generate electricity.

In the polymer electrolyte fuel cell as described above, there may be provided a protective device having a hydrogen sensor (gas detection apparatus) disposed in an exhaust system of a gas discharged from the cathode of the fuel cell, so that supply of fuel is cut off when the hydrogen sensor detects leakage of hydrogen from the anode to the cathode through the solid polymer electrolyte membrane (see JP 6-223850 A, for example).

Among various types of hydrogen sensors known in the art is a catalytic combustible gas sensor. The catalytic combustible gas sensor includes a gas sensing element made of a catalyst (e.g., platinum), and a temperature compensated element. Hydrogen catalytically burns at the gas sensing element when it comes in contact with the catalyst such as platinum; thus, the temperature of the gas sensing element rises relative to the temperature of the temperature compensated element. This generated difference in temperature between the gas sensing element and the temperature compensated element may be represented by a difference in electric resistance. The catalytic combustible gas sensor measures a concentration of hydrogen using such a difference in electric resistance between the gas sensing element and the temperature compensated element.

Exhaust gases discharged from the fuel cell may possibly contain traces of silicon derived from materials of a seal member or the like provided in the exhaust system or piping. Silicon that comes in contact with the catalyst of the gas sensing element may probably poison the catalyst, thus impairing the sensing accuracy of the gas sensing element. With this in view, we, applicants of the instant application, have previously proposed a method for diagnosing a deterioration of a gas sensor (gas detection apparatus), using a first gas sensing element for regular use and a second gas sensing element for use in determination of the deterioration of the first gas sensing element. The first gas sensing element is supplied with electric power continuously, while the second gas sensing element is supplied with electric power intermittently, i.e., normally not energized. This prior invention is disclosed in JP 2004-251862 A (related applications were also published under WO 03/096000 A1, CA 2 485 604 A1, EP 1 505 385 A1 and US 2005/0155405 A1), the disclosure of which is herein incorporated by reference in its entirety.

Typically, air to be supplied as an oxidant to the cathode of the fuel cell is humidified to maintain the ion conductivity of the solid polymer electrolyte membrane, and the exhaust gases discharged from the fuel cell have a moisture content generated by the reaction of hydrogen and oxygen. This may cause condensation on the gas sensing elements on occasions. Since the second gas sensing element of our prior invention described above is not energized in normal times, adhesion of water drops on this second gas sensing element would not only prolong the time required for starting the second gas sensing element but also make the second gas sensing element underperforming, i.e., lowering sensitivity thereof.

Thus, it would be desirable to provide a gas detection apparatus and a method for controlling a gas sensor, by which deterioration of the gas sensor can be detected, and in which the gas sensor can be swiftly started and durability of the gas sensor is enhanced. The present invention has been made against this backdrop.

Illustrative, non-limiting embodiments of the present invention overcome the above disadvantages and other disadvantages not described above. Also, the present invention is not required to overcome the disadvantages described above, and an illustrative, non-limiting embodiment of the present invention may not overcome any of the problems described above.

SUMMARY OF THE INVENTION

It is an aspect of the present invention to provide a gas detection apparatus which includes a first sensing element, a second sensing element, a deterioration determination unit and a power controller. The first sensing element is provided in a first position to measure a concentration of a gas continuously. The second sensing element is provided in a second position to measure the concentration of the gas intermittently, and the second position is in close proximity to the first position. The deterioration determination unit is connected with the first and second sensing elements to make a determination as to whether the first sensing element becomes deteriorated, by comparing output values from the first and second sensing elements. The power controller is configured to supply the second sensing element with electric power throughout waiting periods during which the second sensing element stops measuring the concentration of the gas, whereas an amount of the electric power supplied throughout waiting periods is smaller than that supplied throughout operating periods during which the second sensing element continuously measures the concentration of the gas.

In the above construction, the second sensing element, the output value of which may be used for determination of the deterioration of the first sensing element, is supplied with electric power even during the waiting periods, though the amount of electric power is smaller than that supplied during the operating periods. This makes the second sensing element less prone to a drop in temperature, thus reducing its tendency to cause condensation on the second sensing element. Even when condensation occurs nevertheless, the second sensing element can swiftly resume its operation.

In the above gas detection apparatus, the first and second gas sensing elements may each comprise an element selected from the group consisting of a catalytic combustible sensing element, a semiconductor sensing element, a solid-electrolyte sensing element, an electrochemical sensing element, a field-effect transistor sensing element, a diode sensing element, and an adsorption effect transistor sensing element. The gas to be detected by the first and second gas sensing elements may include a substance selected from the group consisting of combustible hydrocarbon, nitrogen oxide, sulfur oxide, hydrogen sulfide, carbon monoxide, carbon dioxide, halogen, halogenated hydrogen, and ammonia. The first position in which the first sensing element is provided and the second position in which the second sensing element is provided may be in a cabin of a vehicle.

The first sensing element and the second sensing element may each include more than one sensing element. In an exemplary embodiment, in which alarming functionality is provided to notify a user of a deterioration of any of the gas sensing elements, for example, the above gas detection apparatus may further comprise: a third sensing element provided in a third position to measure the concentration of the gas continuously; a fourth sensing element provided in a fourth position to measure the concentration of the gas intermittently, the third position being in close proximity to the fourth position, wherein the deterioration determination unit is further connected with the third and fourth sensing elements to make a determination as to whether the third sensing element becomes deteriorated, by comparing output values from the third and fourth sensing elements; and an alarm unit connected with the deterioration determination unit to issue a warning if the deterioration determination unit makes a determination that at least one of the first and third sensing elements becomes deteriorated.

In yet another aspect of the present invention, there is provided a fuel cell system comprising: a fuel cell having an anode and a cathode, to generate electricity by electrochemical reaction between a hydrogen fuel gas supplied to the anode and an oxygen gas supplied to the cathode; and a gas detection apparatus as described above, wherein the first position in which the first sensing element is provided and the second position in which the second sensing element is provided are in a space through which an exhaust gas discharged from a fuel cell passes. The above fuel cell system may further comprise a diluter provided downstream of the fuel cell to dilute an anode exhaust gas discharged from the anode with a cathode exhaust gas discharged from the cathode, and the first position in which the first sensing element is provided and the second position in which the second sensing element is provided are in a space through which the exhaust gases discharged from the diluter pass.

In yet another aspect of the present invention, there is provided a vehicle comprising: a cabin for accommodating at least one person; and a gas detection apparatus as described above, wherein the first position in which the first sensing element is provided and the second position in which the second sensing element is provided are in the cabin.

A gas detection method as yet another aspect of the present invention comprises: providing a first sensing element in a first position, and a second sensing element in a second position, the second position being in close proximity to the first position; supplying the first sensing element with electric power to allow the first sensing element to measure a concentration of a gas continuously, and supplying the second sensing element with electric power to allow the second sensing element to measure the concentration of the gas intermittently, wherein an amount of electric power supplied to the second sensing element throughout waiting periods during which the second sensing element stops measuring the concentration of the gas is smaller than that supplied to the second sensing element throughout operating periods during which the second sensing element continuously measures the concentration of the gas; and making a determination as to whether the first sensing element becomes deteriorated, by comparing output values from the first and second sensing elements.

In the above gas detection apparatus and method, preferably but not necessarily, the amount of electric power supplied to the second sensing element throughout the waiting periods may include amounts larger than zero. Additionally or alternatively, the amount of electric power supplied to the second sensing element throughout the waiting periods may include amounts that are 30-60% of that supplied throughout operating periods.

In an exemplary embodiment, the first position in which the first sensing element is provided and the second position in which the second sensing element is provided may be in a space through which an exhaust gas discharged from a fuel cell passes. Because the exhaust gas discharged from the fuel cell has a high humidity, the gas detection apparatus and method as described above can produce their advantageous effects conspicuously.

A method for controlling a gas sensor is provided as yet another aspect of the present invention. The gas sensor is comprised of a first sensing element provided in a first position and a second sensing element provided in a second position, to measure a concentration of a gas. The first position and the second position are in close proximity to each other. The method comprises: allowing the first sensing element to measure the concentration of the gas continuously; and allowing the second sensing element to measure the concentration of the gas during operating periods and to stop measuring the concentration of the gas during waiting periods which alternate with the operating periods, by supplying the second sensing element with electric power an amount of which supplied throughout the waiting periods is smaller than that supplied throughout the operating periods.

In the above method, preferably but not necessarily, the amount of electric power supplied to the second sensing element throughout the waiting periods may include amounts larger than zero; additionally or alternatively, the amount of electric power supplied to the second sensing element throughout the waiting periods may include amounts that are 30-60% of that supplied throughout operating periods. In an exemplary embodiment, the first position in which the first sensing element is provided and the second position in which the second sensing element is provided may be in a space through which an exhaust gas discharged from a fuel cell passes.

In an exemplary embodiment of the present invention, there is provided a gas detection apparatus comprising a first sensing element, a second sensing element, a deterioration determination unit, an output switch unit, an alarm unit, and a power controller. The first sensing element is provided in a first position to measure a concentration of a gas continuously; the second sensing element is provided in a second position to measure the concentration of the gas intermittently; and the second position is in close proximity to the first position. The deterioration determination unit is connected with the first sensing element to make a determination as to whether the first sensing element becomes deteriorated, by comparing an output value from the first sensing element with a reference value. The output switch unit and the alarm unit are connected with the deterioration determination unit, and if the deterioration determination unit makes a deterioration determination that the first sensing element becomes deteriorated, the output switch unit switches the concentration of the gas to be output, from the concentration measured by the first sensing element to the concentration measured by the second sensing element, and the alarm unit issues a warning. The power controller is configured to supply the second sensing element with electric power throughout waiting periods during which the second sensing element stops measuring the concentration of the gas, an amount of the electric power supplied throughout waiting periods being smaller than that supplied throughout operating periods during which the second sensing element continuously measures the concentration of the gas. In the above setup, deterioration of the second sensing element may be detected in the same manner, that is, the deterioration determination unit may be further connected with the second sensing element to make a determination as to whether the second sensing element becomes deteriorated, by comparing an output value from the second sensing element with a reference value, and if the deterioration determination unit makes a deterioration determination that the second sensing element becomes deteriorated, and the alarm unit issues a warning.

According to the apparatus and method consistent with the present invention, deterioration of the gas sensor can be detected, the gas sensor can be swiftly started or resumed, and durability of the gas sensor is enhanced.

BRIEF DESCRIPTION OF THE DRAWINGS

The above and other aspects, other advantages and further features of the present invention will become more apparent by describing in detail illustrative, non-limiting embodiments thereof with reference to the accompanying drawings, in which.

DETAILED DESCRIPTION OF THE EXEMPLARY EMBODIMENTS

A detailed description will be given of exemplary embodiments of the present invention with reference made to the drawings as appropriate.

Figure 1:
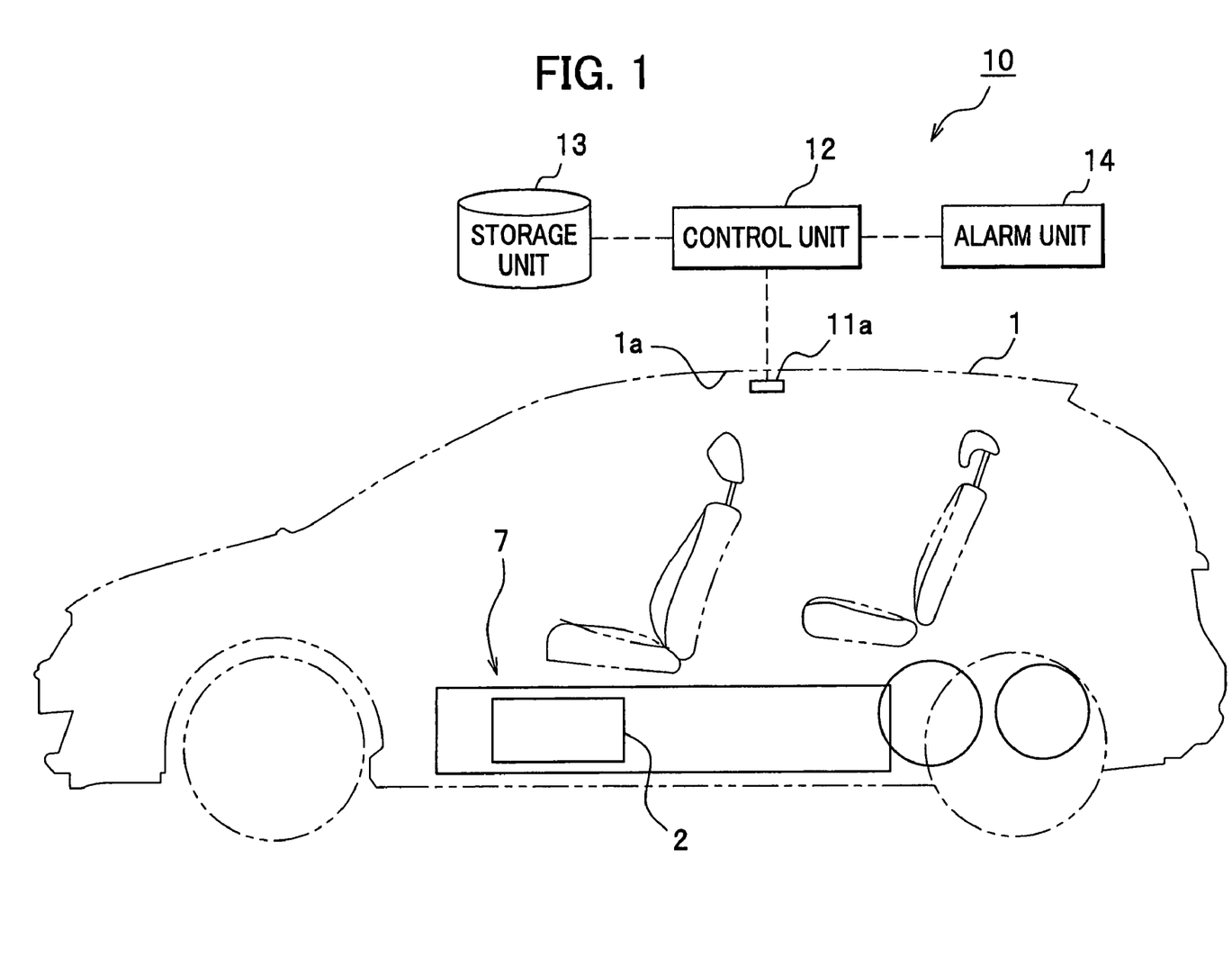
FIG. 1 is a schematic diagram of an automobile (vehicle) as an exemplary embodiment of the present invention.
Figure 2:
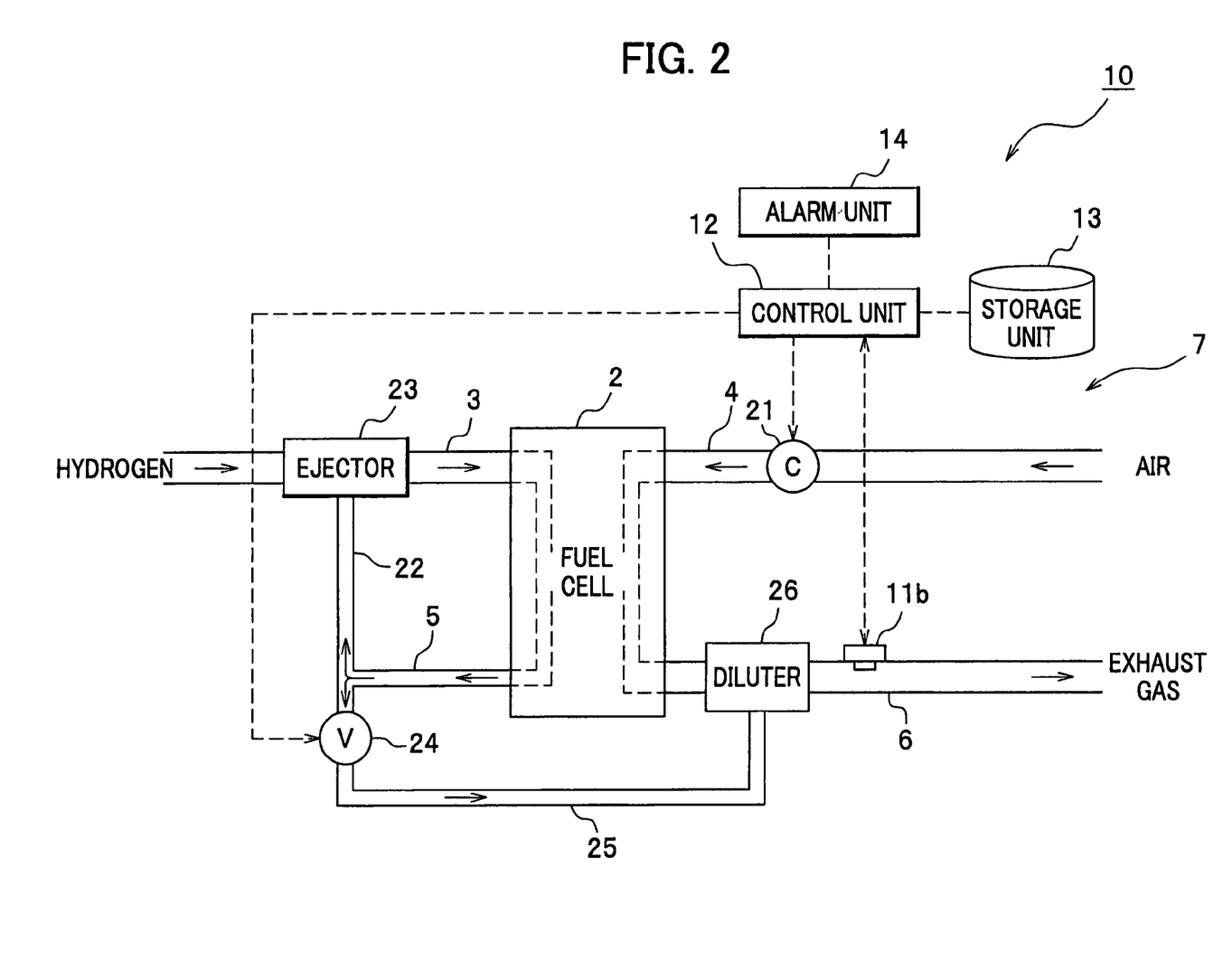
FIG. 2 is a block diagram illustrating a fuel cell system as an exemplary embodiment of the present invention.

A gas detection apparatus 10 according to one embodiment of the present invention has a function of detecting deterioration of a gas sensor, such as a hydrogen sensor 11a for detecting a predetermined concentration (including zero) of hydrogen in a cabin of a vehicle 1 (e.g., fuel-cell electric vehicle) as shown in FIG. 1, and a hydrogen sensor 11b provided in a fuel cell system 7 having a fuel cell 2 for powering the vehicle 1 and pipes 3, 4, 5, 6 connected with the fuel cell 2 as shown in FIG. 2. In one embodiment as illustrated in FIG. 1, the hydrogen sensor 11a is attached on a roof 1a of the vehicle 1; in another embodiment as illustrated in FIG. 2, the hydrogen sensor 11b is provided in an exhaust pipe 6 of a cathode of the fuel cell system 7 (i.e., in a space through which an exhaust gas discharged from the fuel cell 2 passes). In either embodiment, the gas detection apparatus 10 includes a control unit 12, a storage unit 13 and an alarm unit 14, for example.

The control unit 12 is connected with the hydrogen sensor 11a and/or the hydrogen sensor 11b, and makes a determination as to whether the hydrogen sensor 11a and/or the hydrogen sensor 11b become deteriorated, by comparing detection values from the hydrogen sensor 11a and/or the hydrogen sensor 11b with predetermined thresholds stored in the storage unit 13. If the control unit 12 determines that at least one of the hydrogen sensors 11a, 11b has become deteriorated, the control unit 12 causes the alarm unit 14 to issue a warning or the like. The storage unit 13 stores a map, etc. that permits the control unit 13 to look up the predetermined thresholds corresponding to the detection values (output values) of the hydrogen sensors 11a, 11b.

In one embodiment, the fuel cell system 7 as shown in FIG. 2 is installed in the vehicle 1 (e.g., fuel-cell electric vehicle powered by the fuel cell 2) as shown in FIG. 1.

The fuel cell 2 is comprised of a stack of multiple single cells (not shown), each having a pair of separators and an electrolyte membrane electrode assembly sandwiched between the separators. The electrolyte membrane electrode assembly has an anode (fuel pole), a cathode (oxygen pole) and a solid polymer electrolyte membrane (for example, made of a cation exchange membrane) sandwiched between the anode and the cathode.

In the fuel cell 2, hydrogen as a fuel is supplied to the anode through the anode supply pipe 3 from a hydrogen supply unit (not shown), which includes for example a high-pressure hydrogen tank and other components, whereas air as an oxidant is supplied to the cathode through the cathode supply pipe 4 by a compressor 21. Hydrogen at the anode is ionized on a catalytic electrode by catalytic reaction, and the resulting hydrogen ions pass through the adequately humidified solid polymer electrolyte membrane and migrate to the cathode. Electrons produced during this process are carried into an external circuit, and utilized in the form of a direct current electric energy. As the cathode is supplied with air containing oxygen, hydrogen ions, electrons and oxygen react at the cathode to generate water. During this process, the compressor 21 under control of the control unit 12 supplies the fuel cell 2 with air the amount of which is regulated according to the output of the fuel cell 2.

Exhaust gases containing unreacted gases (e.g., hydrogen, air, etc.) are discharged from the fuel cell 2 through the anode exhaust pipe 5 and the cathode exhaust pipe 6.

The exhaust gas containing unreacted hydrogen (anode exhaust gas) is discharged from the anode of the fuel cell 2 through the anode exhaust pipe 5 to a hydrogen circulation line 22, returned by an ejector 23 to the anode supply pipe 3, and supplied again to the anode of the fuel cell 2.

On the other hand, the exhaust gas containing reacted air (cathode exhaust gas) is discharged from the cathode of the fuel cell 2 through the cathode exhaust pipe 6 into the atmosphere.

The cathode exhaust pipe 6 is provided with the hydrogen sensor 11b. In one embodiment where the hydrogen sensor 11b is provided in the cathode exhaust pipe 6 disposed in such an orientation that the cathode exhaust gas flows horizontally, the hydrogen sensor 11b is attached at an upper interior wall of the cathode exhaust pipe 6. The hydrogen sensor 11b is adapted to detect a predetermined concentration (including zero) of hydrogen contained in the cathode exhaust gas passing through the cathode exhaust pipe 6.

As shown in FIG. 2, the anode exhaust pipe 5 is connected via a purge valve 24 to a hydrogen discharge line 25, which is connected to the diluter 26, so that the anode exhaust gas can be discharged through the purge valve 24 to the hydrogen discharge line 25, and introduced through the hydrogen discharge line 25 into the diluter 26.

The diluter 26 is adapted to dilute the anode exhaust gas introduced through the hydrogen discharge line 25 with the anode exhaust gas discharged from the cathode of the fuel cell 2 at an appropriate dilution factor. Thus-diluted anode exhaust gas is discharged from the diluter 26 through the cathode exhaust pipe 6 to the outside.

Downstream of the diluter 26 is provided the hydrogen sensor 11b. The purge valve 24 is regulated to open and close under control of the control unit 12.

Figure 3:
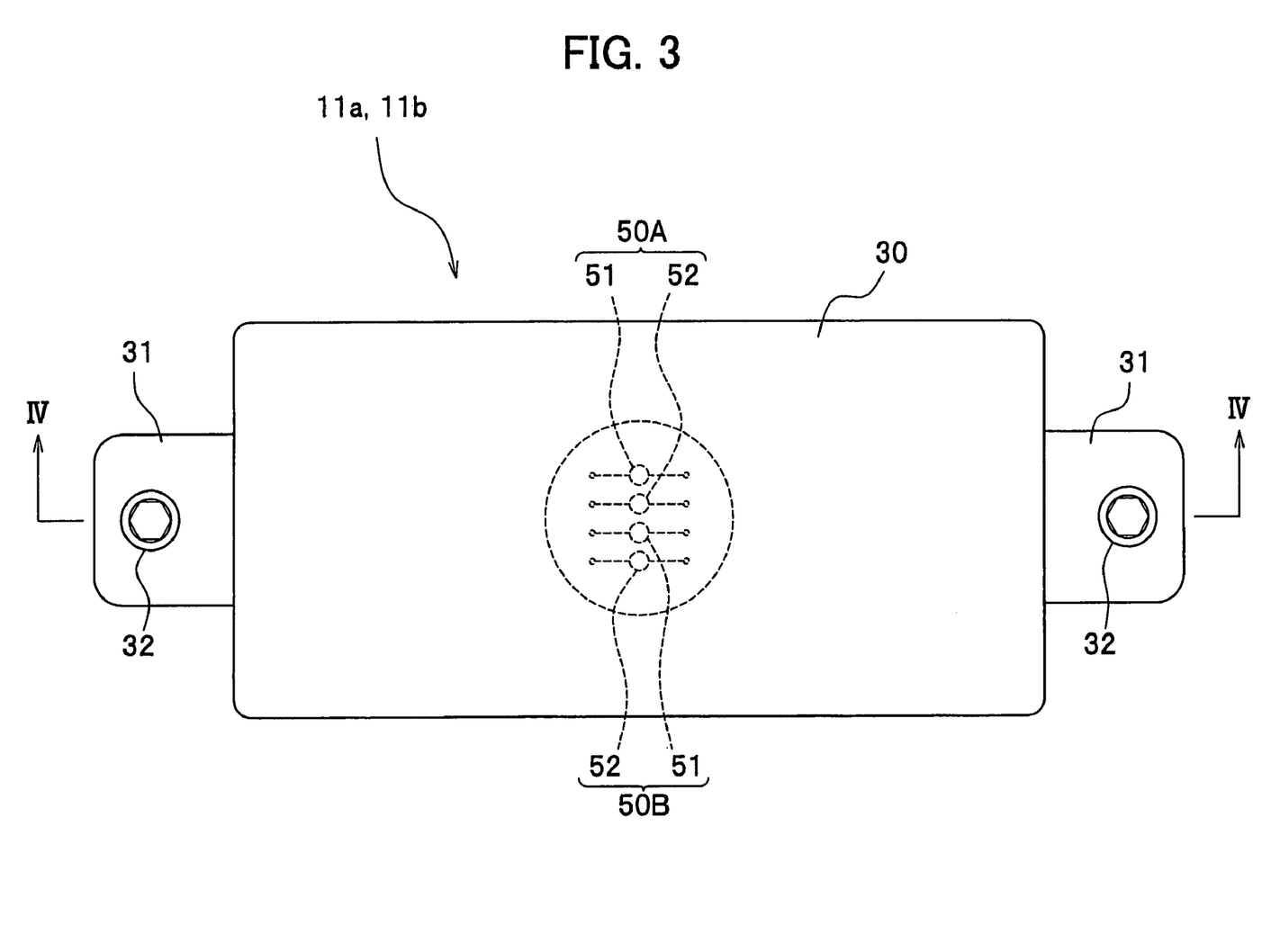
FIG. 3 is a plan view of a hydrogen sensor (gas sensor comprised of sensing elements)
Figure 4:
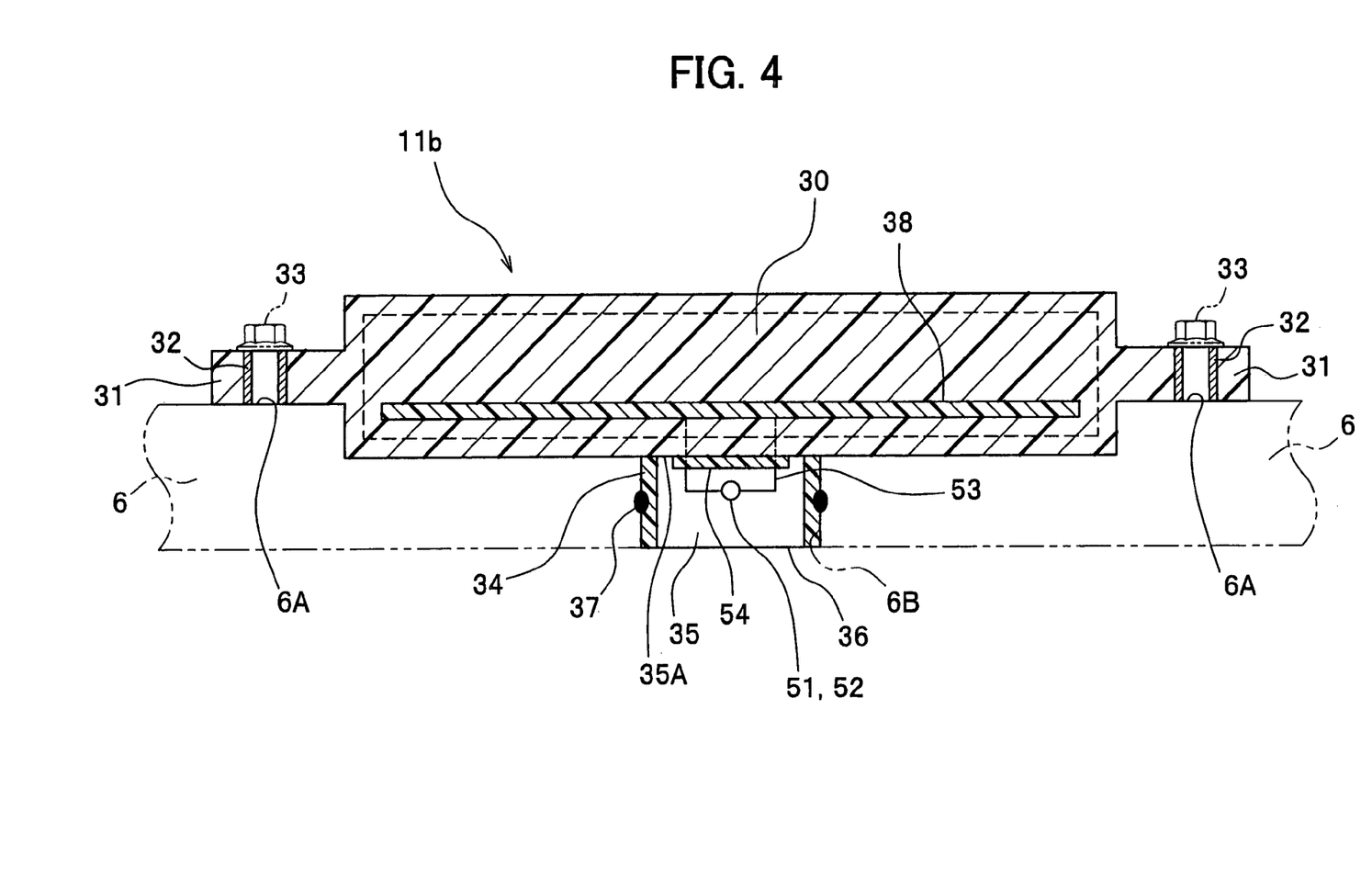
FIG. 4 is a cross-sectional view taken along line IV-IV of FIG. 3.

Turning to FIGS. 3 and 4, a description will be given of the hydrogen sensors 11a, 11b according to an exemplary embodiment of the present invention. In this embodiment, the hydrogen sensors 11a and 11b have the same construction and function; therefore, no duplicate description will be given hereafter for each hydrogen sensor 11a, 11b. As shown in FIG. 3, which is a plan view of the hydrogen sensor 11a, 11b (catalytic combustible sensor), the hydrogen sensor 11a, 11b includes a case 30 shaped substantially like a rectangular parallelepiped. The case 30 is made for example of polyphenylene sulfide, and has two flanges 31 integral with the case 30 and projecting outward perpendicularly from minor sides of the case 30, respectively. Each flange 31 includes a collar 32 embedded therein. When the hydrogen sensor 11a, 11b is mounted on the roof 1a of the vehicle 1 (see FIG. 1) or on the cathode exhaust pipe 6 (see FIG. 4), the flanges 31 are placed on mount seats (not shown) provided on the roof 1a or mount seats 6A provided on the cathode exhaust pipe 6, and a bolt 33 is fitted into the collar 32 of each flange 31 to fasten the flanges 31 to the mount seats.

As shown in FIG. 4, which is a sectional view of the hydrogen sensor 11a, 11b taken along line IV-IV, a cylindrical wall 34 projecting perpendicularly toward inward of the cathode exhaust pipe 6 from one of major sides of the case 30 facing on the cathode exhaust pipe 6 is provided. The brim of the cylindrical wall 34 is open to a space inside the cathode exhaust pipe 6 through which exhaust gases discharged from the fuel cell 2 (and through the diluter 26 in this embodiment) pass, thus forming a gas entrance 36. The inside of the cylindrical wall 34 makes up a space serving as a gas detection chamber 35. A reference sensing element 50A (second sensing element) and a regular-use sensing element 50B (first sensing element) are arranged in the gas detection chamber 35.

On an outer cylindrical surface of the cylindrical wall 34 is provided a seal member 37. The cylindrical wall 34 is fitted in a through hole 6B pierced through the wall of the cathode exhaust pipe 6, so that the hydrogen sensor 11b is attached to the cathode exhaust pipe 6. The seal member 37 maintains contact with both the through hole 6a and the cylindrical wall 34, and thus ensures gas-tightness between the through hole 6a and the cylindrical wall 34.

Figure 5:
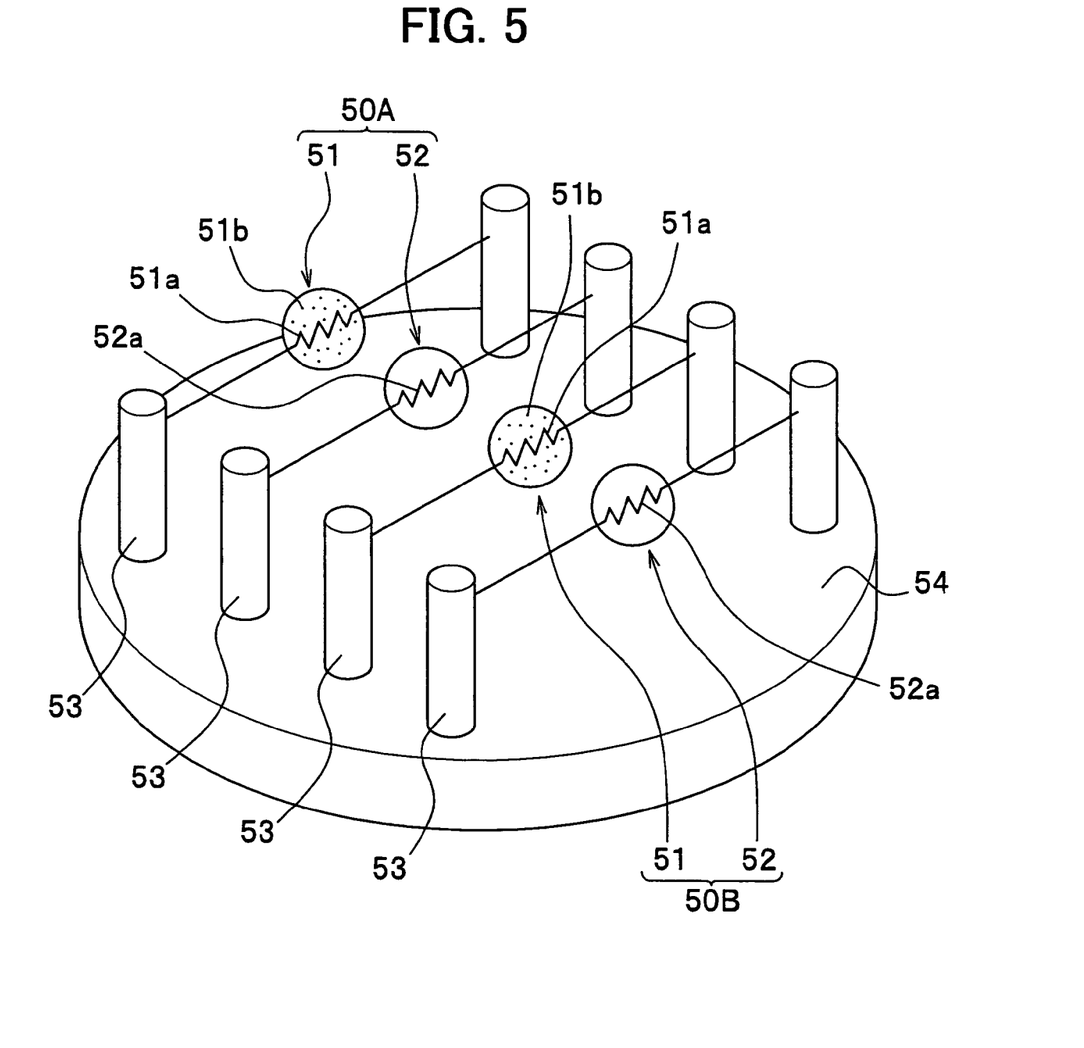
FIG. 5 is a perspective view of sensing elements arranged according to an exemplary embodiment of the present invention.

Referring to FIG. 5, gas sensing elements disposed in a gas sensor according to an exemplary embodiment of the present invention will be described in detail. As shown in FIG. 5, in this embodiment, a reference sensing element 50A and a regular-use sensing element 50B are each comprised of a sensing element 51 and a temperature compensated element 52. The sensing element 51 may be selected from any elements known in the art. In the present embodiment, the sensing element 51 includes a coil-shaped wire 51a and a catalyst 51b carried by a carrier such as alumina, and the coil-shaped wire 51a is coated with the catalyst-carrying carrier. The coil-shaped wire 51a is made of a metal such as platinum having a high coefficient of temperature resistance (expressed as the percentage of change in electric resistance per change in temperature). The catalyst 51 is made of a precious metal that is active in response to a gas to be detected (e.g., hydrogen). The temperature compensated element 52, which is inactive so as not to react with the gas to be detected, includes a coil-shaped wire 52a that is for example equivalent to the coil-shaped wire 51a provided in the sensing element 51, and the surface of the coil-shaped wire 52a is coated with a material such as alumina which carries no catalyst.

The heat of reaction generated when the gas to be detected comes in contact with the catalyst 51b raises the temperature of the sensing element 51, and causes a difference in electric resistance between the sensing element 51 and the temperature compensated element 52, which difference is utilized to measure the concentration of hydrogen. Changes in electric resistance derived from temperature change in the atmosphere are canceled because the temperature compensated element 52 is used as a reference.

The sensing element 51 and the temperature compensated element 52 of each sensing element 50A, 50B are disposed in close proximity to each other, and similarly the reference sensing element 50A and the regular-use sensing element 50B are disposed in close proximity to each other. The sensing elements 51 and the temperature compensated elements 52 are provided in a plane parallel to, and a predetermined distance kept from, a base 54 to which the sensing elements 50A, 50B are mounted. More specifically, the sensing elements 51 and the temperature compensated elements 52, each supported between a pair of posts 53, are suspended at a specific "height" (=the above predetermined distance) over the base 54, as shown in FIG. 5. The phrase "in close proximity" is used to connote that the paired elements (50A and 50B, or 51 and 52) are within a space in which they are surrounded with a substantially homogeneous atmosphere. It is to be understood, for example, that two positions in close proximity to each other are under the same conditions where the gases to be detected (e.g., hydrogen) at these positions should exhibit substantially the same concentration and temperature. Taking, as an example, the concentrations of hydrogen detected by the reference sensing element 50A and the regular-use sensing element 50B, the sensing elements 50A, 50B are positioned so that a deviation of the concentration of hydrogen detected by the regular-use sensing element 50B from the concentration of hydrogen detected by the reference sensing element 50A falls within a predetermined percentage, (e.g., within ±20%, preferably within ±10%, and more preferably within ±5%).

Figure 6:
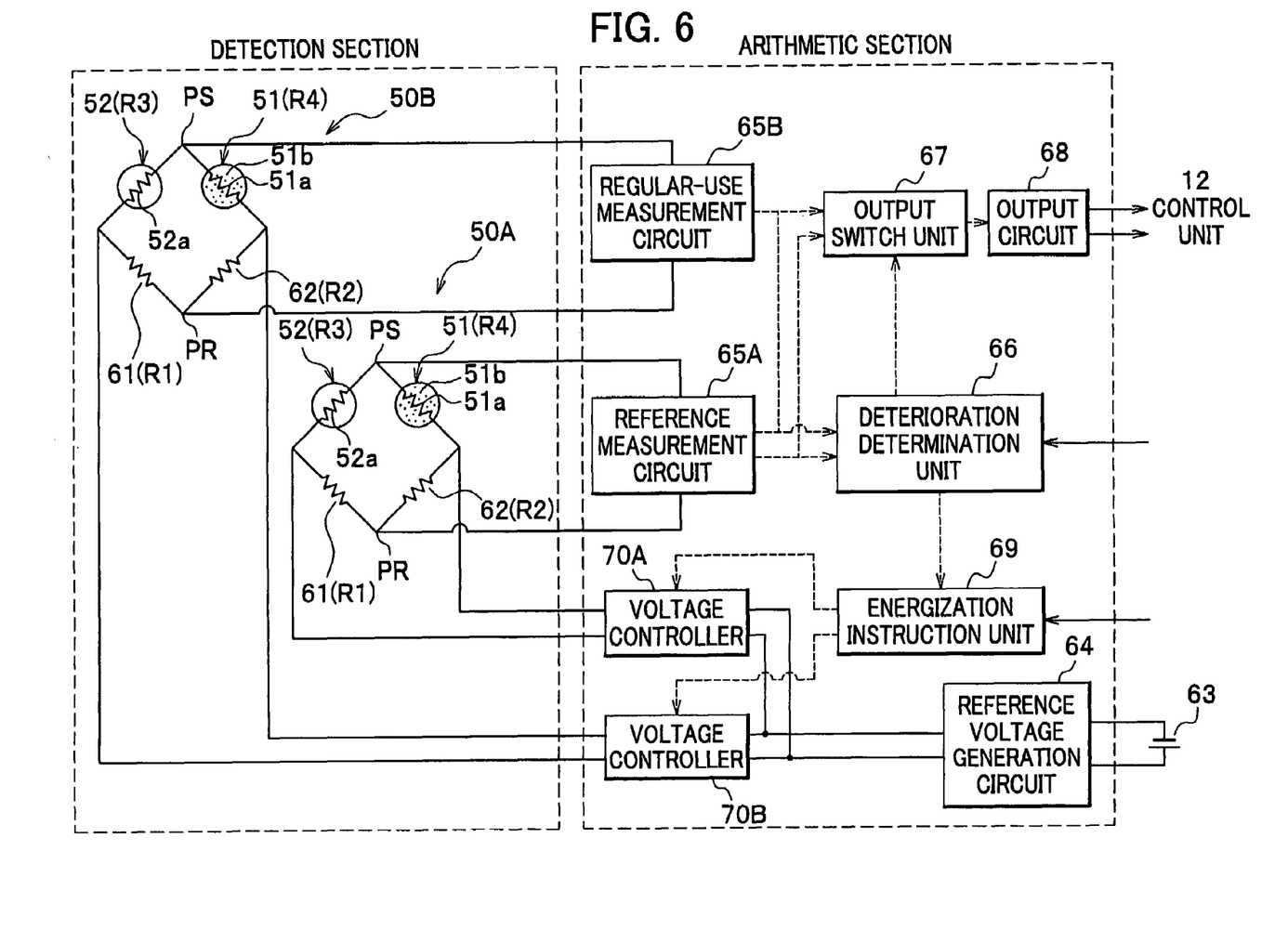
FIG. 6 is a schematic diagram of detection and arithmetic sections of a gas detection apparatus.

The hydrogen sensor 11a, 11b is connected with an electric circuit, as illustrated in FIG. 6, which schematically shows detection and arithmetic sections of the circuit incorporated in the gas detection apparatus 10 to manipulate the outputs of the sensing elements 50A and 50B. The reference sensing element 50A and the regular-use sensing element 50B have the same circuit arrangement, commonly called a Wheatstone bridge, composed of four circuit branches arranged in a square, as shown in FIG. 6, in which: the sensing element 51 (resistor value R4) and the temperature compensated element 52 (resistor value R3) are connected in series; a fixed resistor 61 (resistor value R1) and a fixed resistor 62 (resistor value R2) are connected in series; and these series resistor circuits 51-52 and 61-62 are connected in shunt to a reference voltage generation circuit 64 for applying a constant reference voltage thereto based on the voltage placed by an external power source 63, whereby a bridge circuit is formed for each of the reference sensing element 50A and the regular-use sensing element 50B. In each bridge circuit, between a bridge point PS where the sensing element 51 and the temperature compensated element 52 are connected and a bridge point PR where the fixed resistor 61 and the fixed resistor 62 are connected, a reference or regular-use measurement circuit 65A, 65B are connected. The reference measurement circuit 65A is connected to measure a voltage between the bridge points PS and PR of the bridge circuit for the reference sensing element 50A, while the regular-use measurement circuit 65B is connected to measure a voltage between the bridge points PS and PR of the bridge circuit for the regular-use sensing element 50B.

When no hydrogen (gas to be detected) is present in gases which have been allowed into the gas detection chamber 35 (see FIG. 4), or air which is in the cabin of the vehicle (see FIG. 1), the bridge circuits are kept in a well-balanced condition, so as to satisfy the equation: $R1 \times R4 = R2 \times R3$, and the outputs of the reference measurement circuit 65A and the regular-use measurement circuit 65B are zero. On the other hand, when hydrogen is present in the gases or air, hydrogen in contact with the catalyst 51b of the sensing element 51 burns, and the heat of combustion causes the temperature of the coil-shaped wire 51a to rise, which in turn increases the resistance value R4; however, hydrogen in contact with the temperature compensated element 52, in contrast, fails to burn, and thus the resistance value R3 remains unchanged. As a result, the bridge circuits become unbalanced, and voltages that vary according to the increased concentration of hydrogen are applied to the measurement circuits 65A and 65B, respectively, for measurement.

The measured values of the voltage are output from the measurement circuits 65A and 65B to a deterioration determination unit 66 and an output switch unit 67.

The deterioration determination unit 66 is provided to make a determination as to whether the reference sensing element 50A and/or the regular-use sensing element 50B become deteriorated, by comparing the measured value resulting from detection of the reference sensing element 50A and the measured value resulting from detection of the regular-use sensing element 50B with each other (relative diagnosis), or by comparing the measured value resulting from detection of the reference sensing element 50A and the measured value resulting from detection of the regular-use sensing element 50B independently with a first predetermined reference value and a second predetermined reference value, respectively (absolute diagnosis), as will be described later. The diagnosis results are output to the output switch unit 67, an energization instruction unit 69, and the alarm unit 14.

The output switch unit 67 determines which is to be output, the measured value resulting from detection of the reference sensing element 50A or the measured value resulting from detection of the regular-use sensing element 50B, by using the diagnosis results received from the deterioration determination unit 66, and outputs the one of the values which it has determined to an output circuit 68. Supposing, for example, the output switch unit 67 receives the diagnosis results indicative of deterioration of the regular-use sensing element 50B from the deterioration determination unit 66, the output switch unit 67 switches the output value (the measured value to be output to the output circuit 68) from the value resulting from detection of the regular-use sensing element 50B to the value resulting from detection of the reference sensing element 50A.

The output circuit 68 receives the measured value that has been determined by the output switch unit 67, and outputs the same to the control unit 12, which in turn calculates a concentration of hydrogen based on a map or the like having the concentrations of hydrogen established for all possible values of the voltage to be measured.

The arithmetic section of the circuit as shown in FIG. 6 further includes a voltage controller 70A and a voltage controller 70B. The voltage controller 70A is provided between the reference sensing element 50A and a reference voltage generation circuit 64; the voltage controller 70B is provided between the regular-use sensing element 50B and the reference voltage generation circuit 64. The voltage controllers 70A and 70B are adapted to regulate voltages applied to the sensing elements 50A and 50B, respectively, based upon control instructions received from the energization instruction unit 69.

The energization instruction unit 69 issues control instructions that cause the voltage controllers 70A and 70B to operate in one of predetermined operation modes at times predetermined or determined on the basis of the diagnosis results of deterioration determination received from the deterioration determination unit 66. Operating voltages which the energization instruction unit 69 instructs the voltage controller 70A to generate are changed in accordance with the operation modes, i.e., different between a waiting period during which the reference sensing element 50A stops measuring the concentration of the gas and an operating period during which the reference sensing element 50A continuously measures the concentration of the gas. In particular, the energization instruction unit 69 instructs the voltage controller 70A to apply a voltage to the reference sensing element 50A even during the waiting period which alternates with the operating period. The voltage applied to the reference sensing element 50A throughout the waiting periods is configured to exhibit a predetermined level smaller than that of a voltage applied thereto throughout operating periods (but greater than zero).

Figure 7:
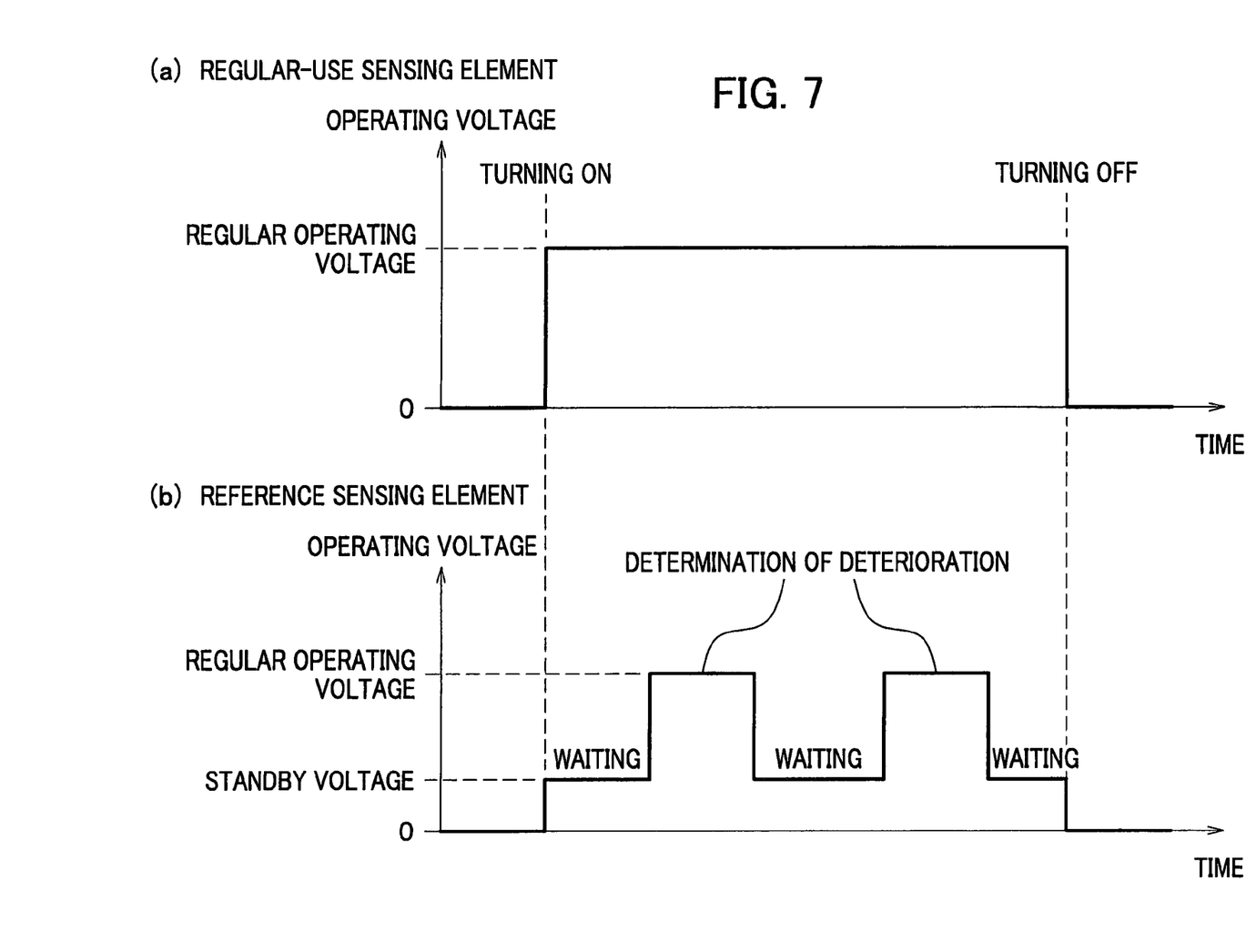
FIG. 7 shows an example of operation of a gas sensor, in which (a) shows an operation of a first sensing element and (b) shows an operation of a second sensing element, according to an exemplary embodiment of the present invention.

To the regular-use sensing element 50B, as shown in FIG. 7(a), is applied a regular operating voltage throughout a period during which the regular-use sensing element 50B continues to measure the concentration of the gas, and application of voltage thereto stops when the regular-use sensing element 50B is turned off.

In contrast, to the reference sensing element 50A, as shown in FIG. 7(b), is applied a regular operating voltage throughout operating periods during which the reference sensing element 50A continues to measure the concentration of the gas for use in determination of deterioration of the regular-use sensing element 50B, and application of voltage thereto stops when the reference sensing element 50A is turned off, like the regular-use sensing element 50B as shown in FIG. 7(a). However, unlike the regular-use sensing element 50B, a standby voltage smaller than the regular operating voltage (but greater than zero) is applied to the reference sensing element 50A throughout waiting periods during which the reference sensing element 50A stops measuring the concentration of the gas, as shown in FIG. 7(b). The operation modes of the voltage controller 70A alternate under control of the energization instruction unit 69 so that the operating periods take place intermittently with the waiting periods placed therebetween.

As described above, a predetermined voltage greater than zero is applied (i.e., electric power is supplied) to the reference sensing element 50A according to the present embodiment, even during the waiting periods; therefore, the temperature of the reference sensing element 50A can be maintained, so that the reference sensing element 50A can be swiftly started or resumed at times when the operating periods start and can be prevented from getting wet because of condensation that would otherwise occur.

Since deterioration of the sensing elements 51 caused by poisoning of the catalyst proceeds only when the sensing elements are energized in a manner according to the applied voltage or supplied electric power as is known in the art, deterioration of the reference sensing element 50A supplied with a limited amount of electric power is slower than that of the regular-use sensing element 50B. Therefore, by comparing an output value of the regular-use sensing element 50B with an output value of the reference sensing element 50A, a determination can be made as to whether the regular-use sensing element 50B becomes deteriorated.

A description will be given of an exemplified operation of the gas detection apparatus 10 as described above with reference to a flowchart shown in FIG. 8.

Figure 8:
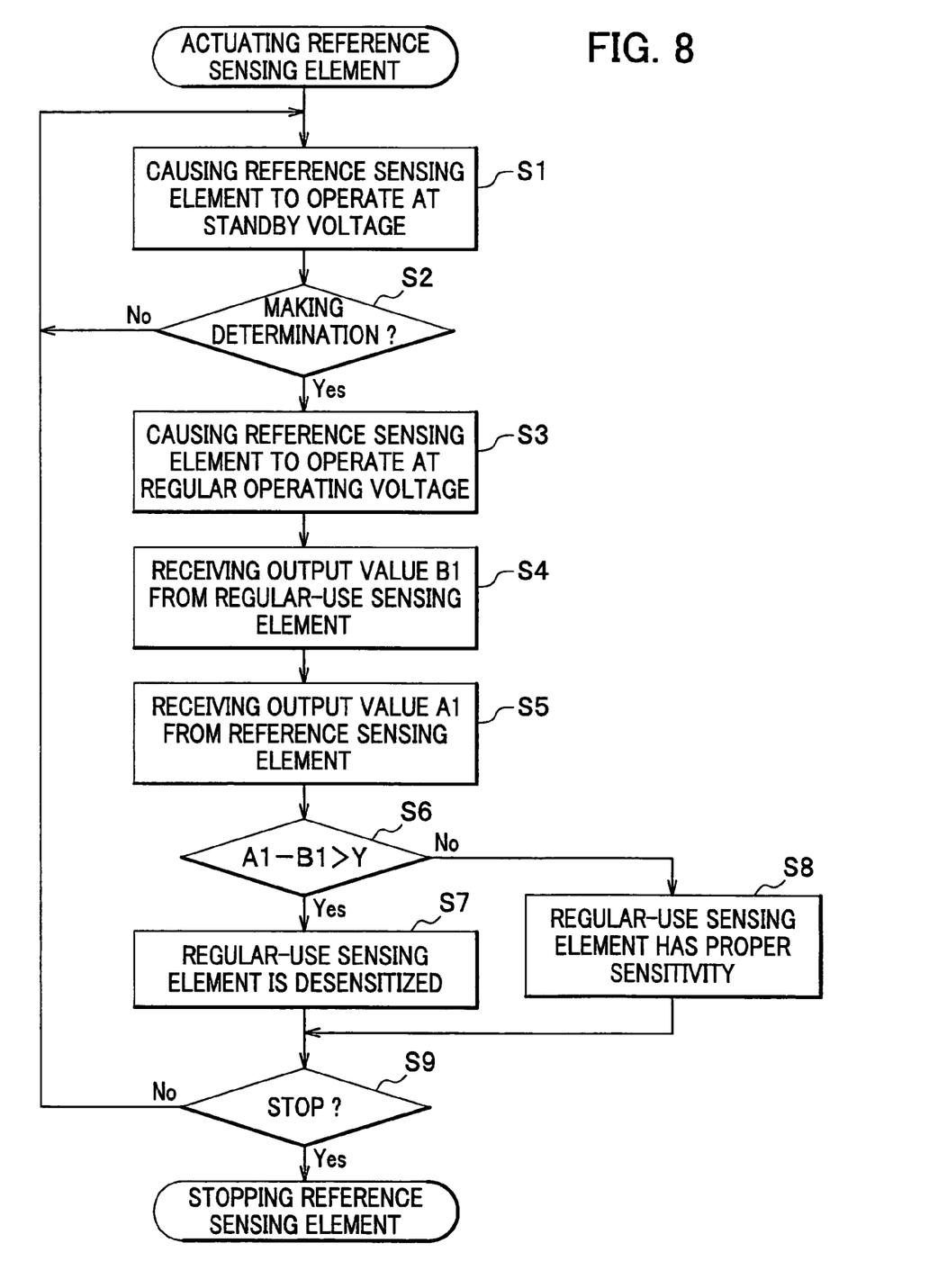
FIG. 8 is a flowchart of an operation of a gas sensor according to an exemplary embodiment of the present invention.

When the reference sensing element 50A is actuated, the reference sensing element 50A operates through application of a standby voltage in accordance with an instruction from the energization instruction unit 69 (S1). The reference sensing element 50A remains in the standby mode (No, S2) until an instruction is issued to make a determination of deterioration. If the instruction is issued to make a determination of deterioration (Yes, S2), the reference sensing element 50A operates through application of a regular operating voltage (S3).

Then, the regular-use measurement circuit 65B receives an output value B1 from the regular-use sensing element 50B (S4), and the reference measurement circuit 65A receives an output value A1 from the reference sensing element 50A (S5). The deterioration determination unit 66 compares a difference between the output value A1 and the output value B1 with a predetermined threshold Y. If the difference is greater than the threshold Y (Yes, S6), the deterioration determination unit 66 determines that the regular-use sensing element 50B has been desensitized (S7), and if the difference is not greater than the threshold Y (No, S6), the deterioration determination unit 66 determines that the regular-use sensing element 50B has a proper sensitivity (S8).

If the control unit 12 issues an instruction to stop the reference sensing element 50A (Yes, S9), the reference sensing element 50A is caused to stop, and if the control unit 12 issues no such instruction (No, S9), the process returns to step S1, causing the reference sensing element 50A to be placed in the standby mode.

Thus, with the gas detection apparatus 10 according to the present embodiment, a voltage greater than zero is applied and electric power is supplied to the reference sensing element 50A even during the waiting periods for which the reference sensing element 50A is in the standby mode; accordingly, the temperature of the reference sensing element 50A can be prevented from lowering. Therefore, the condensation or adhesion of water that would occur at the reference sensing element 50A can be reduced or prevented, with the result that the reference sensing element 50A can be swiftly actuated or resumed at times when the operation of determining deterioration starts. Since adhesion of water to the reference sensing element 50A can be reduced or prevented, durability of the reference sensing element 50A can be increased.

Figure 9:
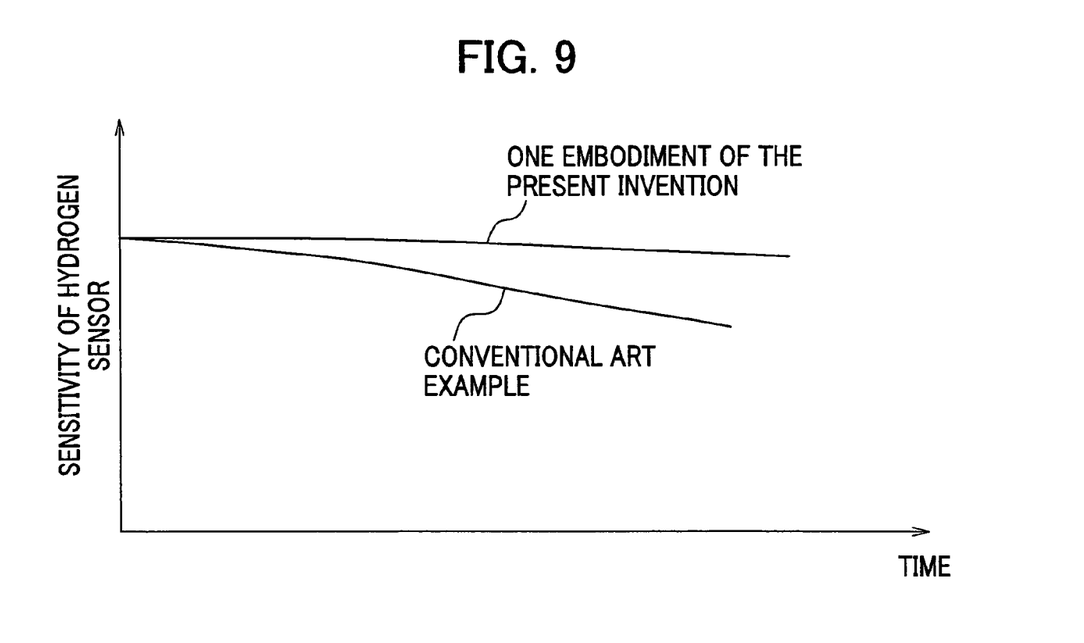
FIG. 9 is a graph showing an advantageous effect of a gas detection apparatus according to an exemplary embodiment of the present invention.

Referring to FIG. 9, which is a graph of time-varying sensitivity of the hydrogen sensor 11b, an advantageous effect of the gas detection apparatus 10 according to the above embodiment of the present invention is described below. In this embodiment, the hydrogen sensor 11b is provided in the cathode exhaust pipe 6 attached at an outlet of the cathode of the fuel cell system 7, and the amount of electric power supplied to the reference sensing element 50A throughout the waiting periods was set at an amount falling within a range of amounts that are 30-60% of that supplied throughout regular operating periods. In this embodiment, even when a long period of time has passed since the hydrogen sensor 11b was actuated, almost no loss of sensitivity was observed; in the conventional example of a similar hydrogen sensor, however, a reference sensing element is ceased to operate, unlike the above embodiment which continuously operates in a standby mode, during periods of time when a determination of deterioration is not made, and the sensitivity of the hydrogen sensor gradually decreased over the course of time.

Although the preferred embodiments of the present invention have been described above, various modifications and changes may be made in the present invention without departing from the spirit and scope thereof.

For example, the number of reference sensing elements 50A and/or regular-use sensing elements 50B provided in the gas detection apparatus 10 is not limited to one, but more than one reference sensing element 50A and more than one regular-use sensing element 50B may be provided, instead. Further, the arrangement of the sensing elements 50A and 50B is not limited to the above exemplified embodiments, but any other arrangement may be adopted as far as they are in close proximity to each other so as to suffice required functions.

Where to provide the gas detection apparatus 10 consistent with the present invention is not limited to the aforementioned embodiments that is provided in a cabin of a vehicle as illustrated in FIG. 1 or in a space through which an exhaust gas discharged from the fuel cell 2 passes as illustrated in FIG. 2; rather, the present invention may be applied to every type of gas detection apparatus for all purposes. The present invention is applicable, preferably but not limited thereto, to particular types of gas detection apparatuses suitable for use in humid surroundings, such as piping in the fuel cell system 7.

The method for determining deterioration of a sensor is not limited to the above-exemplified embodiment; for example, such a method (absolute diagnosis) may be applied that the output value of the regular-use sensing element 50B and/or the output value of the reference sensing element 50A are compared independently with respective specific reference values to detect deterioration of each sensing element 50A, 50B.

The electric power supplied to the reference sensing element 50A during the waiting periods may not necessarily be maintained constant, but may be increased, decreased, or fluctuated as desired.

In the above-described embodiments, the apparatus consistent with the present invention is exemplified by the gas detection apparatus 10 for measuring the concentration of hydrogen gas, but the present invention is not limited thereto. The gas detection apparatuses consistent with the present invention may include a variety of apparatuses having a function of detecting a gaseous component, such as combustible hydrocarbons, $NO_x$, $SO_x$, hydrogen sulfides, carbon monoxides, carbon dioxides, halogen gases, halogenated hydrogen gases, ammonia gases, in a gas.

Although the above-described embodiments use a catalytic combustible sensor as the gas sensor (gas sensing elements), the present invention is not limited to those specific embodiments. Semiconductor gas sensing elements, solid-electrolyte gas sensing elements, electrochemical gas sensing elements, field-effect transistor (FET) gas sensing elements, diode gas sensing elements, adsorption effect transistor (AET) gas sensing elements, and other gas sensing elements or transducers of various types may be employed, instead, as desired.

Figure 10A:
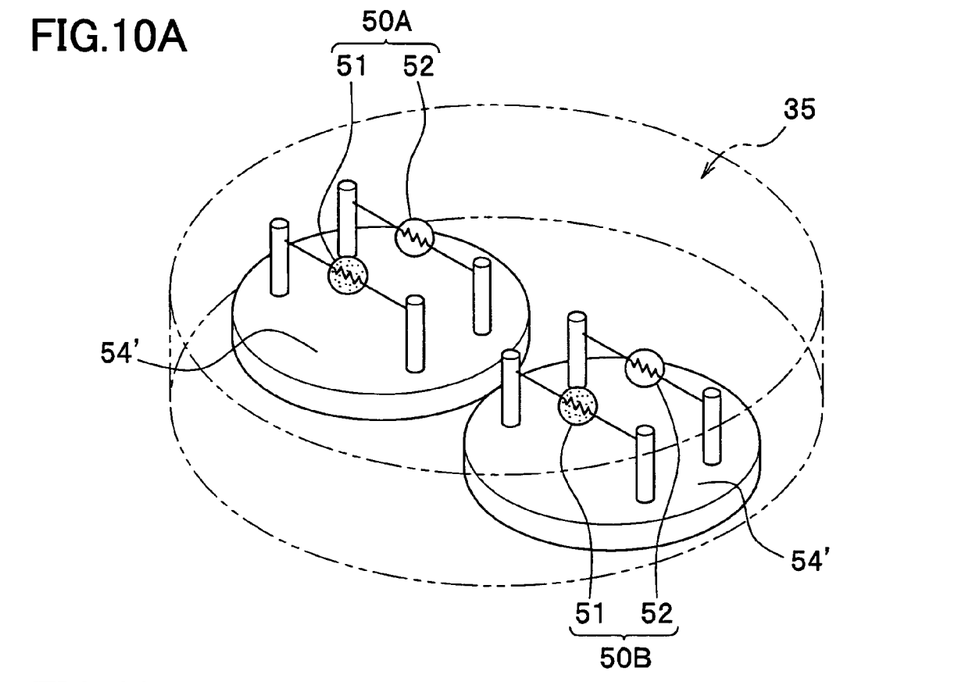
FIG. 10A is a perspective view of sensing elements arranged according to a modified embodiment of the present invention.
Figure 10B:
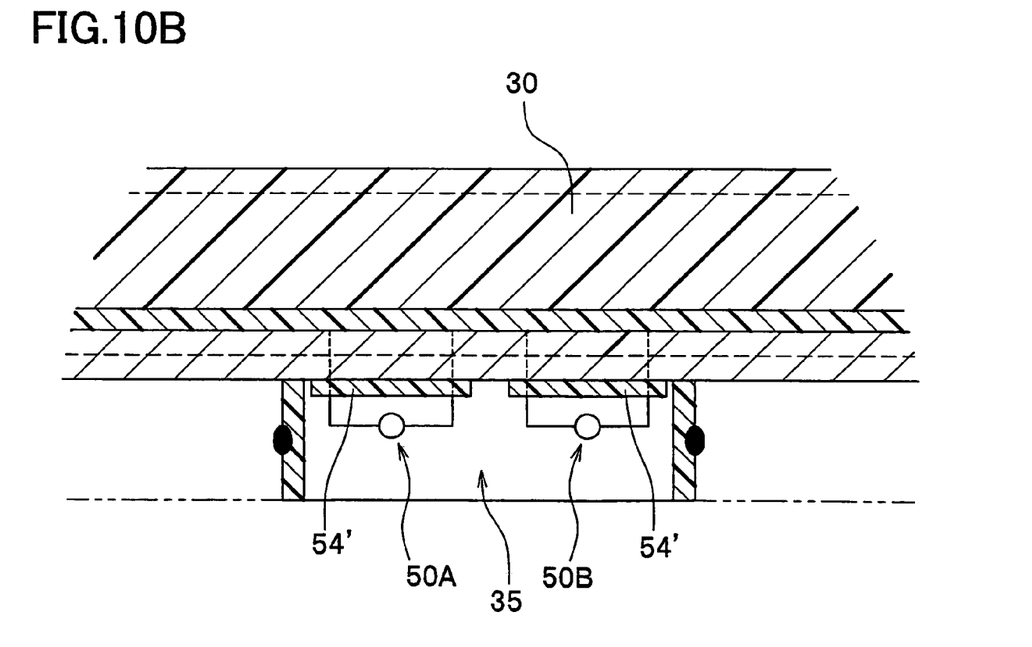
FIG. 10B is a cross-sectional view of a gas sensor incorporating the sensing elements of FIG. 10A.
Figure 11A:
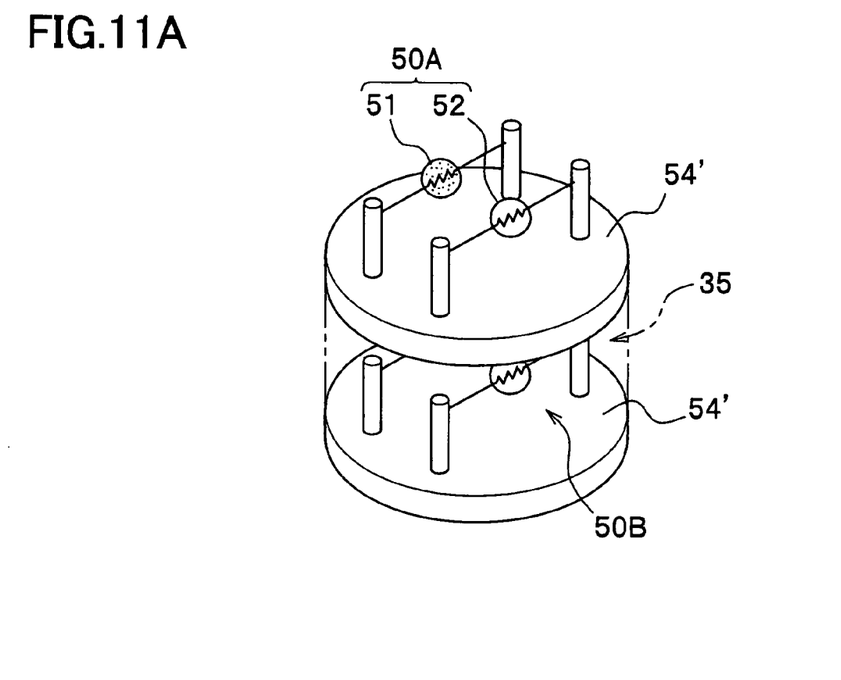
FIG. 11A is a perspective view of sensing elements arranged according to another modified embodiment of the present invention.
Figure 11B:
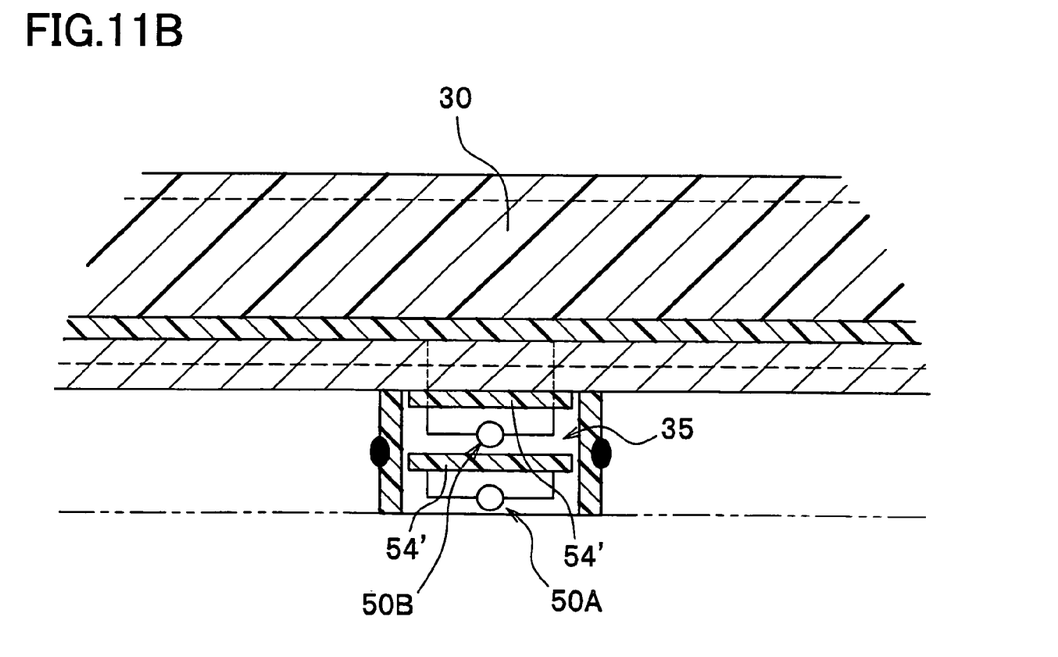
FIG. 11B is a cross-sectional view of a gas sensor incorporating the sensing elements of FIG. 11A.

Furthermore, the arrangement of the sensing elements 50A, 50B is not limited to the above-exemplified embodiments in which two sensing elements 50A, 50B are mounted over a single base 54; any other arrangement may be implemented. For instance, as shown in FIGS. 10A and 10B, the sensing elements 50A and 50B may be mounted separately over two bases 54', which are disposed adjacently in one gas detection chamber 35. Alternatively, as shown in FIGS. 11A and 11B, two bases 54' over which the sensing elements 50A and 50B are mounted separately may be disposed one over the other in one gas detection chamber 35.

What is claimed is:

1. A gas detection apparatus comprising:
   a first sensing element provided in a first position to measure a concentration of a gas continuously;
   a second sensing element provided in a second position to measure the concentration of the gas intermittently, the second position being in close proximity to the first position;
   a deterioration determination unit connected with the first and second sensing elements to make a determination as to whether the first sensing element becomes deteriorated, by comparing output values from the first and second sensing elements; and
   a power controller configured to supply the second sensing element with electric power throughout waiting periods during which the second sensing element stops measuring the concentration of the gas, an amount of the electric power supplied throughout waiting periods being smaller than that supplied throughout operating periods during which the second sensing element continuously measures the concentration of the gas.

2. A gas detection apparatus according to claim 1, wherein the amount of electric power supplied to the second sensing element throughout the waiting periods includes amounts larger than zero.

3. A gas detection apparatus according to claim 1, wherein the amount of electric power supplied to the second sensing element throughout the waiting periods includes amounts that are 30-60% of that supplied throughout operating periods.

4. A gas detection apparatus according to claim 1, wherein the first position in which the first sensing element is provided and the second position in which the second sensing element is provided are in a space through which an exhaust gas discharged from a fuel cell passes.

5. A gas detection method comprising:
   providing a first sensing element in a first position, and a second sensing element in a second position, the second position being in close proximity to the first position;
   supplying the first sensing element with electric power to allow the first sensing element to measure a concentration of a gas continuously, and supplying the second sensing element with electric power to allow the second sensing element to measure the concentration of the gas intermittently, wherein an amount of electric power supplied to the second sensing element throughout waiting periods during which the second sensing element stops measuring the concentration of the gas is smaller than that supplied to the second sensing element throughout operating periods during which the second sensing element continuously measures the concentration of the gas; and
   making a determination as to whether the first sensing element becomes deteriorated, by comparing output values from the first and second sensing elements.

6. A gas detection method according to claim 5, wherein the amount of electric power supplied to the second sensing element throughout the waiting periods includes amounts larger than zero.

7. A gas detection method according to claim 5, wherein the amount of electric power supplied to the second sensing element throughout the waiting periods includes amounts that are 30-60% of that supplied throughout operating periods.

8. A gas detection method according to claim 5, wherein the first position in which the first sensing element is provided and the second position in which the second sensing element is provided are in a space through which an exhaust gas discharged from a fuel cell passes.

9. A method for controlling a gas sensor, which is comprised of a first sensing element provided in a first position and a second sensing element provided in a second position to measure a concentration of a gas, the first position and the second position being in close proximity to each other, the method comprising:
   allowing the first sensing element to measure the concentration of the gas continuously; and
   allowing the second sensing element to measure the concentration of the gas during operating periods and to stop measuring the concentration of the gas during waiting periods which alternate with the operating periods, by supplying the second sensing element with electric power an amount of which supplied throughout the waiting periods is smaller than that supplied throughout the operating periods.

10. The method according to claim 9, wherein the amount of electric power supplied to the second sensing element throughout the waiting periods includes amounts larger than zero.

11. The method according to claim 9, wherein the amount of electric power supplied to the second sensing element throughout the waiting periods includes amounts that are 30-60% of that supplied throughout operating periods.

12. The method according to claim 9, wherein the first position in which the first sensing element is provided and the second position in which the second sensing element is provided are in a space through which an exhaust gas discharged from a fuel cell passes.

13. A gas detection apparatus according to claim 1, wherein the first and second gas sensing elements each comprise an element selected from the group consisting of a catalytic combustible sensing element, a semiconductor sensing element, a solid-electrolyte sensing element, an electrochemical sensing element, a field-effect transistor sensing element, a diode sensing element, and an adsorption effect transistor sensing element.

14. A gas detection apparatus according to claim 1, wherein the gas to be detected by the first and second gas sensing elements is a substance selected from the group consisting of combustible hydrocarbon, nitrogen oxide, sulfur oxide, hydrogen sulfide, carbon monoxide, carbon dioxide, halogen, halogenated hydrogen, and ammonia.

15. A gas detection apparatus according to claim 1, wherein the first position in which the first sensing element is provided and the second position in which the second sensing element is provided are in a cabin of a vehicle.

16. A gas detection apparatus according to claim 1, further comprising:
a third sensing element provided in a third position to measure the concentration of the gas continuously;
a fourth sensing element provided in a fourth position to measure the concentration of the gas intermittently, the third position being in close proximity to the fourth position, wherein the deterioration determination unit is further connected with the third and fourth sensing elements to make a determination as to whether the third sensing element becomes deteriorated, by comparing output values from the third and fourth sensing elements; and
an alarm unit connected with the deterioration determination unit to issue a warning if the deterioration determination unit makes a determination that at least one of the first and third sensing elements becomes deteriorated.

17. A fuel cell system comprising:
a fuel cell having an anode and a cathode, to generate electricity by electrochemical reaction between a hydrogen fuel gas supplied to the anode and an oxygen gas supplied to the cathode; and
a gas detection apparatus according to claim 1, wherein the first position in which the first sensing element is provided and the second position in which the second sensing element is provided are in a space through which an exhaust gas discharged from a fuel cell passes.

18. A fuel cell system according to claim 17, further comprising a diluter provided downstream of the fuel cell to dilute an anode exhaust gas discharged from the anode with a cathode exhaust gas discharged from the cathode,
wherein the first position in which the first sensing element is provided and the second position in which the second sensing element is provided are in a space through which the exhaust gases discharged from the diluter pass.

19. A vehicle comprising:
a cabin for accommodating at least one person; and
a gas detection apparatus according to claim 1, wherein the first position in which the first sensing element is provided and the second position in which the second sensing element is provided are in the cabin.

20. A gas detection apparatus comprising:
a first sensing element provided in a first position to measure a concentration of a gas continuously;
a second sensing element provided in a second position to measure the concentration of the gas intermittently, the second position being in close proximity to the first position;
a deterioration determination unit connected with the first sensing element to make a determination as to whether the first sensing element becomes deteriorated, by comparing an output value from the first sensing element with a reference value;
an output switch unit connected with the deterioration determination unit to switch the concentration of the gas to be output, from the concentration measured by the first sensing element to the concentration measured by the second sensing element if the deterioration determination unit makes a deterioration determination that the first sensing element becomes deteriorated,
an alarm unit connected with the deterioration determination unit to issue a warning if the deterioration determination unit makes the deterioration determination; and
a power controller configured to supply the second sensing element with electric power throughout waiting periods during which the second sensing element stops measuring the concentration of the gas, an amount of the electric power supplied throughout waiting periods being smaller than that supplied throughout operating periods during which the second sensing element continuously measures the concentration of the gas.

* * * * *